US010314941B2

(12) United States Patent
McKinley et al.

(10) Patent No.: US 10,314,941 B2
(45) Date of Patent: Jun. 11, 2019

(54) PREVENTATIVE THERAPY FOR POST-TRAUMATIC OSTEOARTHRITIS

(71) Applicant: University of Iowa Research Foundation, Iowa City, IA (US)

(72) Inventors: Todd O. McKinley, Indianapolis, IN (US); James A. Martin, Iowa City, IA (US); Mitchell Coleman, Iowa City, IA (US); Tae-Hong Lim, Coralville, IA (US); Marc Brouillette, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/895,518

(22) Filed: Feb. 13, 2018

(65) Prior Publication Data

US 2018/0169298 A1 Jun. 21, 2018

Related U.S. Application Data

(63) Continuation of application No. PCT/US2016/047360, filed on Aug. 17, 2016.

(60) Provisional application No. 62/207,059, filed on Aug. 19, 2015.

(51) Int. Cl.
| | |
|---|---|
| *A61K 9/00* | (2006.01) |
| *A61K 9/06* | (2006.01) |
| *C08L 5/08* | (2006.01) |
| *A61K 47/34* | (2017.01) |
| *A61K 47/36* | (2006.01) |
| *A61K 47/38* | (2006.01) |
| *A61L 27/26* | (2006.01) |
| *A61L 27/50* | (2006.01) |
| *A61L 27/52* | (2006.01) |
| *A61L 27/54* | (2006.01) |
| *A61P 19/02* | (2006.01) |
| *C08L 71/02* | (2006.01) |
| *A61K 31/155* | (2006.01) |
| *A61K 31/515* | (2006.01) |

(52) U.S. Cl.
CPC ........... *A61L 27/26* (2013.01); *A61K 9/0024* (2013.01); *A61K 9/06* (2013.01); *A61K 31/155* (2013.01); *A61K 31/515* (2013.01); *A61K 47/34* (2013.01); *A61K 47/36* (2013.01); *A61K 47/38* (2013.01); *A61L 27/50* (2013.01); *A61L 27/52* (2013.01); *A61L 27/54* (2013.01); *A61P 19/02* (2018.01); *A61L 2300/434* (2013.01); *A61L 2400/06* (2013.01); *A61L 2430/24* (2013.01)

(58) Field of Classification Search
CPC .......... A61L 27/26; A61L 27/50; A61L 27/52; A61L 27/54; A61L 2300/434; A61L 2400/06; A61L 2430/24; A61K 47/38; A61K 31/155; A61K 9/0024; A61K 9/06; A61K 47/34; A61K 31/515; A61K 47/36; A61P 19/02

See application file for complete search history.

(56) References Cited

U.S. PATENT DOCUMENTS

| | | | |
|---|---|---|---|
| 8,759,402 B2 | 6/2014 | Gottlieb et al. | |
| 2007/0292478 A1 | 12/2007 | Youri | |
| 2015/0071904 A1 | 3/2015 | Collins et al. | |

FOREIGN PATENT DOCUMENTS

| | | |
|---|---|---|
| CN | 108136070 A | 6/2018 |
| EP | 1496037 A | 1/2005 |
| WO | WO-2006047279 A2 | 5/2006 |
| WO | WO-2010061005 A1 | 6/2010 |
| WO | WO-2013171736 A1 | 11/2013 |
| WO | WO-2017031214 A1 | 2/2017 |

OTHER PUBLICATIONS

Tsuyoshi (EP1496037 A1) (Year: 2005).*
Mckinley et al. ("Mitochondrial Based Treatments that Prevent Post-Traumatic Osteoarthritis in a Translational Large Animal Intraarticular Fracture Survival Model", 2013). (Year: 2013).*
Martin, James, "Blocking Acute Oxidative Insult to Chondrocytes Prevents Post-Traumatic Osteoarthritis in a Porcine Model of Tibial Plafond Fracture (Abstract of Presentation)", Extremity and War Injuries XI Conference, Washington DC, (2016), 1pg.
"International Application Serial No. PCT/US2016/047360, International Search Report dated Nov. 21, 2016", 4 pgs.
"International Application Serial No. PCT/US2016/047360, Written Opinion dated Nov. 21, 2016", 8 pgs.
L, Perraud, "Accumulation of Free ADP-ribose from Mitochondria Mediates Oxidative Stress-induced Gating of TRPM2 Cation Channels", Journal of Biological Chemistry, vol. 280, No. 7, (Feb. 18, 2005), 6138-6148.
Mohammed, M Mohammed, et al., "Evaluation of the Clinical use of Metformin or Pioglitazone in Combination with Meloxicam in Patients with Knee Osteoarthritis; using Knee Injury and Osteoarthritis outcome Score", Iraqi J Pharm Sci, vol. 23, No. 2 (Jan. 14, 2015), 13-26.

(Continued)

*Primary Examiner* — Robert A Wax
*Assistant Examiner* — Quanglong N Truong
(74) *Attorney, Agent, or Firm* — Schwegman Lundberg & Woessner, P.A.

(57) ABSTRACT

Compositions comprising a reverse-temperature sensitive hydrogel comprising a biopolymer such as a polysaccharide and a synthetic polymer, and a compound in an amount that reversibly inhibits respiratory enzyme complex I, and methods of using the composition, are provided.

25 Claims, 4 Drawing Sheets

(56) References Cited

OTHER PUBLICATIONS

Mustafa, Naziroglu, "New Molecular Mechanisms on the Activation of TRPM2 Channels by Oxidative Stress and ADP-Ribose", Neurochemical Research, Kluwer Academic Publishers-Plenum Publishers, NE vol. 32, No. 11, (Jun. 12, 2007), 1990-2001.

Todd, O McKinley, et al., "Mitochondrial Based Treatments that Prevent Post-Traumatic Osteoarthritis in a Translational Large Animal intraarticular Fracture Survival Model Principal Investigator: Distribution Statement: Approved for Public Release; Distribution Uniimited", [Online] retrieved from the Internet:: <URL:http://www.dti c.mi l/get-tr-doc/pdf? Loc ati on=U2&doc=GetTRDoc.pdf&AD=ADA592443>, (Jan. 28, 2014).

"International Application Serial No. PCT/US2016/047360, Supplementary International Search Report dated Nov. 30, 2017", 37 pgs.

"International Application Serial No. PCTUS2016047360 International Preliminary Report on Patentability dated Mar. 1, 2018", 10 pgs.

Brouillette, M J, et al., "Strain-Dependent Oxidant Release in Articular Cartilage Originates from Mitochondria", Biomech Model Mechanobiol. 13(3), (Jun. 2014), 565-572.

Brouillette, Marc James, "Static Compressive Stress Induces Mitochondrial Oxidant Production in Articular Cartilage (Thesis)", A thesis submitted in partial fulfillment of the requirements for the Master of Science degree in Biomedical Engineering in the Graduate College of the University of Iowa, (May 2012), 51 pgs.

Coleman, M, "Complex I inhibition after intra-articular fracture prevents rapid progression of osteoarthritis in a porcine model (Abstract with graphs)", 63rd Annual Meeting of the Orthopaedic Research Society, San Diego, California, (2017), 1 pg.

Coleman, M, et al., "Complex I Inhibition after Intra-articular Fracture Prevents Rapid Progression of Osteoarthritis in a Porcine Model (Poster)", 63rd Annual Meeting of the Orthopaedic Research Society, San Diego, California, (2017), 1 pg.

Coleman, M, "Differential Effects of Superoxide Dismutase Mimetics after Mechanical Overload of Articular Cartilage (Abstract)", Antioxidants, 6(4), (2017), 2 pgs.

Coleman, M, et al., "Injurious Loading of Articular Cartilage Compromises Chondrocyte Respiratory Function (Abstract)", Arthritis Rheumatol, 68(3, (2016), 2 pgs.

Coleman, M, et al., "Intraarticular Administration of N-Acetylcysteine Alleviates Acute Oxidative Stress Following Intraarticular Fracture (Abstract)", Oberly Symposium, Iowa City, IA, (2015), 1 pg.

Coleman, M, "Intraarticular Administration of N-Acetylcysteine and Glycyrrhizin Alleviates Acute Oxidative Stress Following Intraarticular Fracture (Abstract)", Orthopaedic Research Society Annual Meeting, Las Vegas, Nevada, (2015), 1 pg.

Coleman, M, "Intraarticular Administration of N-Acetylcysteine and Glycyrrhizin Alleviates Acute Oxidative Stress Following Intraarticular Fracture (Poster)", Orthopaedic Research Society Annual Meeting, Las Vegas, Nevada, (2015), 1 pg.

Coleman, M, "Intraarticular Administration of N-Acetylcysteine Prevents Progression of Post-Traumatic Osteoarthritis in a Large Animal Model of Intraarticular Fracture (Abstract)", Society for Free Radical Biology and Medicine, Boston, Massachusetts, (2015), 1 pg.

Coleman, M, "Intraarticular Administration of N-Acetylcysteine Prevents Progression of Post-Traumatic Osteoarthritis in a Large Animal Model of Intraarticular Fracture (Presentation)", Society for Free Radical Biology and Medicine, Boston, Massachusetts, (2015), 29 pgs.

Coleman, M, et al., "N-Acetylcysteine Prevents Acute Chondrocyte Injury and Dysfunction Associated with Osteoarthritic Progression after Intraarticular Fracture (Poster)", Military Health System Research Symposium, Fort Lauderdale, Florida, (2015), 1 pg.

Coleman, M, "Osteoarthritis in Porcine Intraarticular Fracture Model Reveals Mitochondrial Features Similar to Human Disease (Abstract)", Annual Meeting of the Orthopaedic Research Society, Orlando, Florida, (2016), 1 pg.

Coleman, M, "Osteoarthritis in Porcine Intraarticular Fracture Model Reveals Mitochondrial Features Similar to Human Disease (Poster)", Annual Meeting of the Orthopaedic Research Society, Orlando, Florida, (2016), 1 pg.

Coleman, M, et al., "Overloading Healthy Articular Cartilage Induces Mitochondrial Dysfunction Reminiscent of Late Stage Osteoarthritis (Abstract)", Orthopaedic Research Society Annual Meeting, New Orleans, Louisiana, (2014), 1 pg.

Coleman, M, et al., "Overloading Healthy Articular Cartilage Induces Mitochondrial Dysfunction Reminiscent of Late Stage Osteoarthritis (Poster)", Orthopaedic Research Society Annual Meeting, New Orleans, Louisiana, (2014), 1 pg.

Coleman, M, et al., "Targeting mitochondrial responses to intraarticular fracture to prevent posttraumatic osteoarthritis", Science Translational Medicine, 10, Issue 427, (Feb. 2018), 15 pgs.

Coleman, Mitchell, et al., "Complex I Inhibition after Intra-articular Fracture Prevents Rapid Progression of Osteoarthritis in a Porcine Model (Abstract)", OARSI, (2017), 1 pg.

Coleman, Mitchell, et al., "Differential Effects of Superoxide Dismutase Mimetics after Mechanical Overload of Articular Cartilage", Antioxidants 6(4), (2017), 10 pgs.

Coleman, Mitchell, et al., "Loading of Articular Cartilage Compromises Chondrocyte Respiratory Function", Arthritis Rheumatol, 68(3), (Mar. 2016), 662-671.

Coleman, Mitchell, "Mitochondrial Responses to Intraarticular Fracture are a Disease-Modifying Target for Post-Traumatic Osteoarthritis Prevention", Nature Medicine, (Mar. 2017).

Coleman, Mitchell, et al., "N-Acetylcysteine Prevents Acute Chondrocyte Injury and Dysfunction Associated with Osteoarthritic Progression after Intraarticular Fracture (Abstract)", Military Health System Research Symposium, Fort Lauderdale, Florida, (2015), 1 pg.

Coleman, Mitchell, "Three Critical Considerations for Translating Redox Therapies: Location, Location, Location (Presentation)", (2017), 55 pgs.

Compton, Jocelyn, et al., "Sirtuin-1 Augments Chondrogenic Progenitor Cell Activity in an Acute Cartilage Injury Model (Poster)", ORS, (2018), 1 pg.

Goetz, Jessica, et al., "Time-Dependent Loss of Mitochondrial Function Precedes Progressive Histologic Cartilage Degeneration in a Rabbit Meniscal Destabilization Model", J Orthop Res., 35(3), (2017), 590-599.

Goodwin, Wendy, et al., "Rotenone Prevents Impact-Induced Chondrocyte Death", Journal of Orthopaedic Research 28(8), (2010), 1057-1063.

Jubeck, Brian, et al., "Promotion of Articular Cartilage Matrix Vesicle Mineralization by Type I Collagen", Arthritis Rheum. 58(9), (2008), 2809-2817.

Martin, James, et al., "N-Acetylcysteine Inhibits Post-Impact Chondrocyte Death in Osteochondral Explants", Journal of Bone and Joint Surgery, vol. 91-A, No. 8, (2009), 1890-1897.

Sauter, Ellen, et al., "Cytoskeletal Dissolution Blocks Oxidant Release and Cell Death in Injured Cartilage", Journal of Orthopaedic Research, 30(4), (2012), 593-598.

Sigaeva, N, et al., "Chemical modification of hyaluronic acid and its application medicine (with machine translation)", vol. 17. No. 3. Herald of Bashkir University, (2012), 1220-1241.

Wolff, K, "Mechanical Stress and ATP Synthesis Are Coupled by Mitochondrial Oxidants in Articular Cartilage (Abstract)", J Orthop Res 31(2), (2013), 191-196.

Wolff, Katherine, et al., "Mechanical Stress and ATP Synthesis Are Coupled by Mitochondrial Oxidants in Articular Cartilage", Journal of Orthopaedic Research, 31(2), (2013), 191-196.

Badwaik, V., et al., "Efficient pDNA Delivery Using Cationic 2-Hydroxypropyl-β-Cyclodextrin Pluronic-Based Polyrotaxanes", Macromol Biosci.; 16(1):63-73, (Jan. 2016), (Abstract Only).

Bahadur, A, et al., "NaCl-triggered self-assembly of hydrophilic poloxamine block copolymers", Int J Pharm.; 494(1):453-62, (Oct. 15, 2015), (Abstract Only).

Brunori, M., et al., "Nitric oxide and the respiratory enzyme", Biochim Biophys Acta, 1757(9-10), (Sep.-Oct. 2006), (Abstract Only).

(56) References Cited

OTHER PUBLICATIONS

Glinka, Y., et al., "Nature of inhibition of mitochondrial respiratory complex I by 6-Hydroxydopamine", J Neurochem. 66(5), (May 1996), (Abstract Only).

Hao, S., et al., "Mitochondrion-Targeted Peptide SS-31 Inhibited Oxidized Low-Density Lipoproteins-Induced Foam Cell Formation through both ROS Scavenging and Inhibition of Cholesterol Influx in RAW264.7 Cells", Molecules.; 20(12):21287-97, (Dec. 1, 2015), (Abstract Only).

James, AD, et al., "The Plasma Membrane Calcium Pump in Pancreatic Cancer Cells Exhibiting the Warburg Effect Relies on Glycolytic ATP", J Biol Chem.; 290(41): 24760-71, (Oct. 2015), (Abstract Only).

Kerkhofs, S., et al., "Self-Assembly of Pluronic F127-Silica Spherical Core-Shell Nanoparticles in Cubic Close-Packed Structures", Chem Mater.; 27(15):5161-5169, (Aug. 11, 2015), (Abstract Only).

Moncada, PS, "Nitric Oxide and Oxygen: Actions and Interactions in Health and Disease", Redox Biol.; 5:421, (Aug. 2015), (Abstract Only).

Müller, M., et al., "Nanostructured Pluronic hydrogels as bioinks for 3D bioprinting", Biofabrication.; 7(3), (Aug. 2015), (Abstract Only).

Novakofski, KD, et al., "Joint-dependent response to impact and implications for posttraumatic", Osteoarthritis Cartilage: 23(7):1130-7, (Jul. 2015), (Abstract Only).

Roma, MI, et al., "Tetronic® 904-containing polymeric micelles overcome the overexpression of ABCG2 in the blood-brain barrier of rats and boost the penetration of the antiretroviral efavirenz into the CNS", Nanomedicine (Lond).; 10(15):2325-37, (2015), (Abstract Only).

Sandez-Macho, I., et al., "Interaction of poloxamine block copolymers with lipid membranes: Role of copolymer structure and membrane cholesterol content", Colloids Surf B Biointerfaces; 133:270-7, (Sep. 2015), (Abstract Only).

Sharma, S., et al., "Investigating the role of Pluronic-g-Cationic polyelectrolyte as functional stabilizer for nanocrystals: Impact on Paclitaxel oral bioavailability and tumor growth", Acta Biomater.; 26:169-83, (Oct. 2015), (Abstract Only).

Zhang, W., et al., "Involvement of ROS-mediated mitochondrial dysfunction and SIRT3 down-regulation in tris(2-chloroethyl)phosphate-induced cell cycle arrest", Toxicol Res (Camb).; 5(2):461-470, (Dec. 14, 2015), (Abstract Only).

Fakhari, A, et al., "Applications and emerging trends of hyaluronic acid in tissue engineering, as a dermal filler and in osteoarthritis treatment (Abstract)", Acta Biomater, 9:7081, (2013), 1 pg.

Koh, Minsoo, et al., "A novel metformin derivative, HL010183, inhibits proliferation and invasion of triple-negative breast cancer cells (Abstract)", vol. 21, Issue 8, (2013), 2 pgs.

Sogame, Yoshihisa, "A comparison of uptake of metformin and phenformin mediated by hOCT1 in human hepatocytes (Abstract)", Biopharm. Drug Dispos., 30:476, (2009), 2 pgs.

"European Application Serial No. 16757452.4, Response filed Oct. 8, 2018 to Communication Pursuant to Rules 161(1) and 162 EPC dated Mar. 29, 2018", w English Claims, 14 pgs.

"Chinese Application Serial No. 201680056186.X, Voluntary Amendment filed Oct. 8, 2018", w English Claims, 13 pgs.

"European Application Serial No. 16757452.4, Communication pursuant to Article 94(3) EPC dated Mar. 14, 2019", 6 pgs.

\* cited by examiner

PREVENTATIVE THERAPY FOR POST-TRAUMATIC OSTEOARTHRITIS

CLAIM FOR PRIORITY

This application is a continuation of and claims the benefit of priority to International Application No. PCT/US2016/047360, filed Aug. 17, 2016, which claims the benefit of priority to U.S. Provisional Patent Application Ser. No. 62/207,059, filed Aug. 19, 2015, the disclosure of which is incorporated by reference herein.

STATEMENT OF GOVERNMENT RIGHTS

This invention was made with government support under grant W81XWH-11-1-0583 awarded by the Department of Defense. The government has certain rights in the invention.

BACKGROUND

The pain, immobility, and general disability associated with osteoarthritis are familiar to most people who reach old age. Post-traumatic osteoarthritis (PTOA) is a profoundly accelerated form of arthritis associated with traumatic injuries to joint articular surfaces, leading to disease progression well before patients are considered good candidates for joint replacement approaches common to orthopaedic medicine. Because patients are often injured relatively young and there are presently no viable alternatives to joint replacement, patients with PTOA often suffer disability and morbidity comparable to chronic heart disease patients.

Natural methods for treating PTOA include decreasing load and stress on the injured joint or increasing comfort and functionality. For example, weight loss, low impact exercise, and strengthening muscles surrounding the joint may improve PTOA. However, these approaches do not cure or prevent PTOA and may not be fully effective.

Non-steroidal, anti-inflammatory medicines (NSAIDS) are used to decrease pain and inflammation associated with PTOA, although NSAIDs can cause stomach irritation and kidney, liver or heart problems. Moreover, NSAIDs likely do not prevent PTOA. Antioxidants, another class of compounds used to treat PTOA, stabilize or deactivate reactive oxygen species (ROS) before they attack cells. Nevertheless, there is skepticism about the benefit of antioxidants and there are potentially harmful side effects if anti-oxidants are taken in excess.

Other methods used to treat PTOA include the administration of cortisone and hylamers which act like artificial joint fluid after injection. However, cortisone can cause elevation of heart rate and blood sugar and should not be given too often. In addition, cortisone is not preventative. While corticosteroid injections are anti-inflammatory, the potential benefit or adverse effects of that injection for traumatic injury have not been resolved. Another approach is the use of platelet-rich plasma injections.

Injection of a patient's own platelets leads to release of growth factors and attraction of regenerative cells to the site of injury. This type of injection is not preventative and does not work for all PTOA patients. Moreover, details on dosage, frequency of injection, and other important parameters have yet to be worked out for platelet rich plasma administration. A further type of injection is an amniotic membrane stem cell injection. While this injection is anti-inflammatory, thus providing pain relief, and results in replacement of damaged cells due to release of growth factors, it is not preventative and does not target ROS.

If non-surgical methods are ineffective, surgical methods may be employed to restore the joint after PTOA. The surgery may include cleaning out, reconstructing or replacing the worn out joint surfaces. As with other surgeries, there can be surgical complications, e.g., infection and damage to surrounding structures, blood clots, heart attack, and stroke, and the eventual wearing out or loosening of implants.

SUMMARY

The present disclosure provides an injectable composite hydrogel comprising a polysaccharide, e.g., a natural polysaccharide such as hyaluronic acid, hydroxypropylcellulose, karya gum (KG), guar gum (GUG), or gellan gum (GEG), a semi-synthetic polysaccharide or a synthetic polysaccharide, and a synthetic polymer, e.g., F127, whose reverse-thermal properties cause the composite to become firm once injected (preventing leakage from the site of injection such as a joint), and a compound useful to prevent, inhibit or treat PTOA. In one embodiment, the compound reversibly inhibits the respiratory enzyme complex I, a key mediator of chondrocyte injury after impact. In one embodiment, the hydrogel comprises an effective amount of amobarbital, e.g., from about 0.25 mM to about 50 mM or about 1.25 mM to about 10 mM, metformin (N,N,-dimethylbiguanide) a biguanide derivative, N,N-diethylbiguanide, N,N,-dipropylbiguanide, phenformin (Sogame et al., *Biopharm. Drug Dispos.*, 30:476 (2009)), or HL010183 (Koh et al., *Bioorg. Med. Chem.*, 21:2305 (2013)), or adenosine diphosphate ribose or a derivative thereof. In one embodiment, the volume administered is about 0.1 mL to about 15 mL, e.g., about 1 mL to about 10 mL or about 2 mL to about 5 mL. The combination of materials in the hydrogel offers a practical advantage, for instance, in enabling health care providers to protect articular tissue acutely after injury. Also, the use of compounds that reversibly inhibit the respiratory enzyme complex I to alter articular cartilage provides for chondroprotection after injury and eventual reestablishment of normal activity of the respiratory enzyme complex I.

The disclosure provides an injectable composition comprising a composite reverse-temperature sensitive hydrogel comprising a biopolymer, such as a polysaccharide, and a synthetic polymer, and a compound in an amount that optionally reversibly inhibits respiratory enzyme complex I. In one embodiment, the hydrogel includes about 0.2 wt/vol to about 4% wt/vol HA In one embodiment, the polysaccharide comprises hyaluronic acid. In one embodiment, the synthetic polymer comprises a poloxamer, e.g., F127. In one embodiment, the hydrogel includes about 15% wt/vol to about 20% wt/vol F127. In one embodiment, the compound comprises amobarbital. In one embodiment, the amount of the compound in the hydrogel inhibits mitochondrial dysfunction or chondrocyte energy dysfunction. In one embodiment, the compound scavenges mitochondrial oxidants or prevents their formation, or stimulates glycolytic ATP production In one embodiment, the hydrogel comprises N-isopropyl acrylamide polymer, ethylhydroxyethylcellulose, poly(etheylene oxide-b-propylene oxide-b-ethylene oxide), poloxamers, PLURONICS® polymers, poly(ethylene glycol)/poly(D,L-lactic acid-co-glycolic acid) block co-polymers, polysaccharides, alginate, polyphosphazines, polyacrylates, TETRONICS™ polymers, or polyethylene oxide-polypropylene glycol block copolymers. In one embodiment, the polysaccharride comprises hyaluronic acid of about or greater than 1.5 M Dalton. In one embodiment, the MW is about 1,600,000 to 3,200,000, or about 1,900,000 to 3,900,000.

In one embodiment, the polysaccharide comprises hydroxypropylcellulose, karya gum (KG), guar gum (GUG), or gellan gum (GEG). In one embodiment, the polysaccharide is present in the hydrogel at about 0.2% (wt/vol) to about 1.0% (wt/vol).

In one embodiment, the composition is a reverse temperature-sensitive hydrogel (one that is non-viscous at "low" temperature, e.g., at or below room temperature, e.g., about 70° F. or less. The low initial viscosity allows the hydrogel to coat all the cartilage surfaces through the joint before it sets (i.e., the viscosity increases at temperatures above room temperature, e.g., about 80° F. or greater including human body temperature such as about 98° F.), which provides for superior retention in the joint and substantially improves the bioavailablity of the compound dissolved in the gel. Reverse temperature-sensitive hydrogels, which have initial viscosities of about 100 to about 160 or about 80 to about 200, e.g., about 120 to about 140, Pascal Seconds, may be administered using a 22 to 24 gauge needle, e.g., a 22 gauge needle. In contrast, non-reverse temperature-sensitive hydrogels require large bore needles and do not evenly distribute in the joint due to their high initial viscosity.

Also provided is a method to prevent or inhibit chondrocyte death and improve chondrocyte function after injury in a mammal. The method includes administering an effective amount of the composition to a mammal having the injury. Further provided is a method to prevent or inhibit post-traumatic osteoarthritis in a mammal. The method includes administering an effective amount of the composition a mammal at risk of posttraumatic osteoarthritis. In one embodiment, the composition comprises hyaluronic acid. In one embodiment, the composition comprises F127. In one embodiment, the composition comprises amobarbital. In one embodiment, the amount administered inhibits mitochondrial dysfunction or chondrocyte energy dysfunction. In one embodiment, the compound administered scavenges mitochondrial oxidants or prevent their formation, in addition to stimulating glycolytic ATP production. In one embodiment, the administration is within 1, 2, 3, 4 or 5 days of the injury. In one embodiment, the mammal has an injured joint. In one embodiment, the administration is with 1, 2, 3, 4, 5, 6, 7, 8, 9, 10 11, or 12 hours of the injury.

DETAILED DESCRIPTION OF THE FIGURES

FIG. 1 is a schematic of the electron transport chain. Electrons from donor molecules are transferred through protein complexes. As electrons are transferred, hydrogen ions are pumped across the inner membrane of the mitochondria, and as the hydrogen atoms fall back over the inner membrane, they generate ATP.

DETAILED DESCRIPTION

Definitions

"Hydrogel" as used herein means a water insoluble, naturally or chemically-induced cross-linked, three-dimensional network of polymer chains plus water that fills the voids between polymer.

Cartilage, Electron Transport and PTOA

Articular cartilage is the smooth, white tissue that covers the ends of bones where they come together to form joints. It allows the bones to glide over each other with very little friction, and acts as a cushion. Injured, inflamed, or damaged cartilage does not heal itself well due to lack of a blood supply, resulting in symptoms such as pain and limited movement leading to joint damage and deformity. Chondrocytes are cells found in cartilage connective tissue they produce and maintain the cartilage matrix. Under normal circumstances, cartilage wears down over time and chondrocytes replace and repair it as needed.

Figure 1:
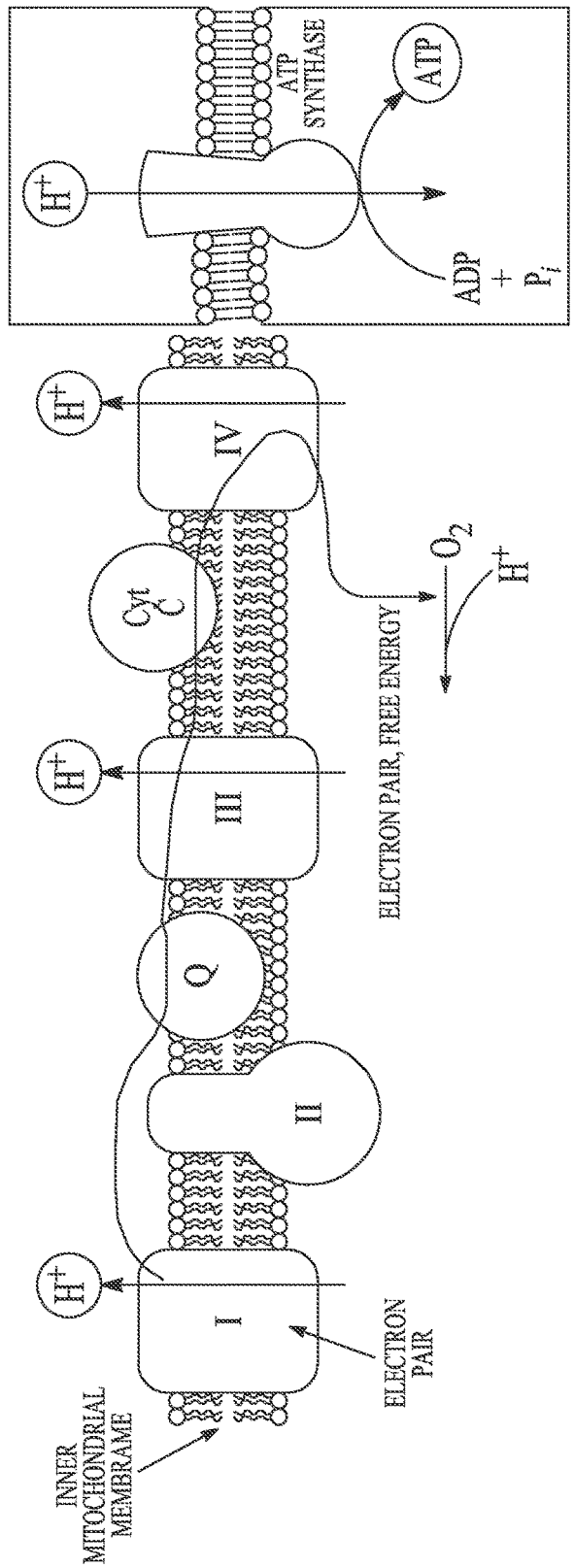
Figure 2:
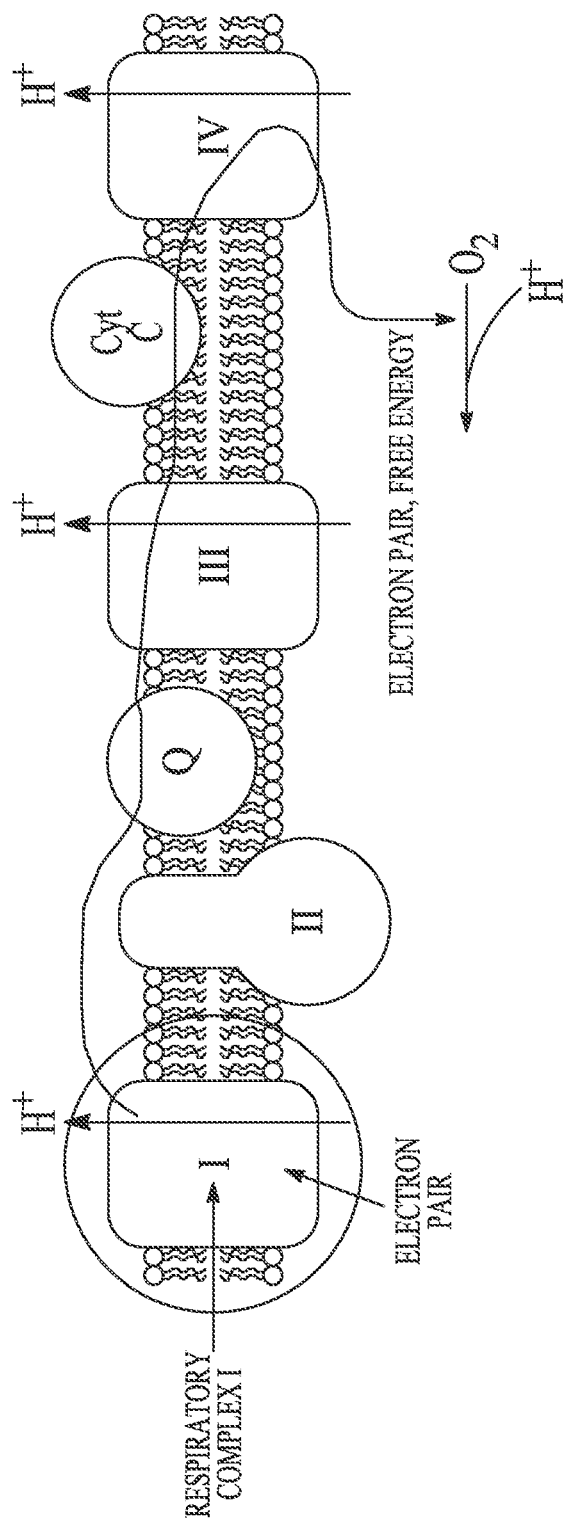
FIG. 2 is a schematic of reactive oxygen species production.
Figure 3:
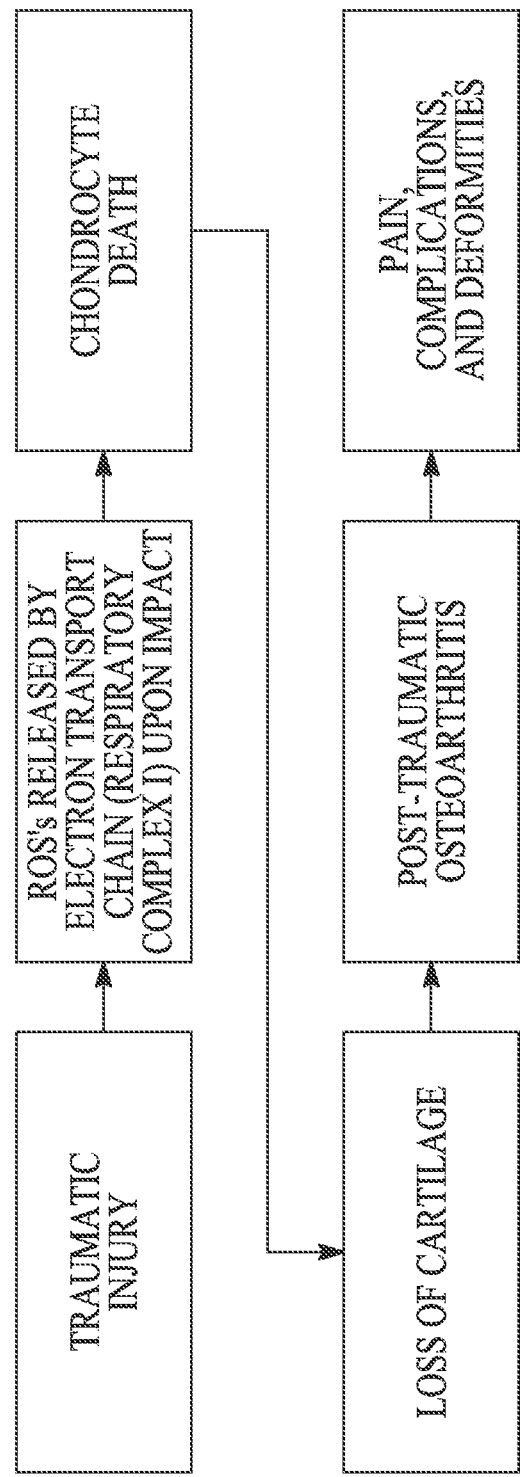
FIG. 3 is a schematic of steps in the progression to post-traumatic osteoarthritis.

Chondrocyes, like all cells, contain mitochondria. Mitochondria generate ATP through the Electron Transport Chain (ETC) (FIG. 1). Sometimes, harmful substances called reactive oxygen species (ROS) (FIG. 2) are created through the ATP generation process and are formed by Respiratory Complex I in the Electron Transport Chain. ROS can act as signaling molecules and signal healthy chondrocytes to undergo apoptosis (cell suicide), depending on the severity and length of exposure, which leads to osteoarthritis.

Osteoarthritis is wearing out of joint surface cartilage over time. Post-traumatic osteoarthritis (PTOA) is wearing out of a joint that has had any kind of physical injury. PTOA is a debilitating consequence of intraarticular fractures. Patient outcomes after intraarticular fractures have not improved significantly in spite of improved surgical techniques. PTOA is relatively common: As of 2006 approximately 12% of the overall prevalence of symptomatic OA was attributable to PTOA of the hip, knee, or ankle. This corresponds to approximately 5.6 million individuals in the United States being affected by PTOA. The corresponding aggregate financial burden specifically of PTOA is $3.06 billion annually, or approximately 0.15% of the total U.S. health care direct cost outlay.

Compositions and Methods to Prevent, Inhibit or Treat PTOA

Inhibiting electron transport and associated oxidant production by chondrocytes after impact injuries associated with PTOA prevents cell death and dysfunction. Accordingly, by muting chondrocyte mitochondrial metabolism acutely after traumatic injury using compounds that inhibit respiratory enzyme complex I (and also decrease ROS) that are delivered intra-articularly in a hydrogel vehicle, the treatment is confined to the joint capsule and prevents leaking out of any joint disruptions present. This allows controlled local delivery of an effective pharmaceutical in a manner that minimizes exposure to the rest of the body. For example, amobarbital is a barbiturate derivative used to produce relaxation, sleep, anesthesia, and anticonvulsant effects. It inhibits respiratory complex I, leading to a decrease in ROS. Because the effect of amobarbital in inhibiting mitochondrial electron transport is reversible, unlike rotenone or other more toxic alternatives, transient manipulation of chondrocyte metabolism in this manner can prevent chondrocyte injury and death, as well as subsequent disease, while avoiding toxic insult to the patient due to return of oxidative metabolism.

The present compositions and method are useful to prevent, inhibit or treat PTOA, and may substantially lower or eliminate treatment costs and morbidities associated with other more invasive approaches that require multiple surgical procedures and/or cell harvests.

Hydrogels and Polymers Useful in Hydrogels

Hydrogels can be classified as those with crosslinked networks having permanent junctions or those with physical networks having transient junctions arising from polymer chain entanglements or physical interactions, e.g., ionic interactions, hydrogen bonds or hydrophobic interactions. Natural materials useful in hydrogels include natural polymers, which are biocompatible, biodegradable, support cellular activities, and may include proteins like fibrin, collagen or gelatin, and/or polysaccharides like hyaluronic acid, starch, alginate or agarose. Synthetic polymers useful in hydrogels are prepared by chemical polymerization and include by way of example poloxamers, acrylic acid, hydroxyethyl-methacrylate (HEMA), vinyl acetate, and methacrylic acid (MAA).

Various methods may be used to prepare hydrogels, e.g., crosslinkers, copolymerization of monomers using multifunctional co-monomer, cross linking of linear polymers by irradiation or by chemical compounds. Monomers contain an ionizable group that can be ionized or can undergo a substitution reaction after the polymerization is completed. Exemplary crosslinkers are glutaraldehyde, calcium chloride and oxidized konjac glucomannan (DAK).

Some classes of hydrogels include (a) homopolymeric hydrogels which are derived from a single species of monomer. Homopolymers may have cross-linked skeletal structure depending on the nature of the monomer and polymerization technique; (b) copolymeric hydrogels which are comprised of two or more different monomer species with at least one hydrophilic component, arranged in a random, block or alternating configuration along the chain of the polymer network; (c) multipolymer interpenetrating polymeric hydrogel (IPN) which is made of two independent cross-linked synthetic and/or natural polymer components, contained in a network form. In semi-IPN hydrogel, one component is a cross-linked polymer and other component is a non-cross-linked polymer.

Biodegradable hydrogels as a delivery vehicle have the advantage of being environmentally friendly to the human body (due to their biodegradability) and of providing more predictable, controlled release of the impregnated drugs. Hydrogels are of special interest in biological environments since they have a high water content as is found in body tissue and are highly biocompatible. Hydrogels and natural biological gels have hydrodynamic properties similar to that of cells and tissues. Hydrogels minimize mechanical and frictional irritation to the surrounding tissue because of their soft and compliant nature. Therefore, hydrogels provide a far more user-friendly delivery vehicle than the relatively hydrophobic carriers like silicone, or vinyl acetate.

Biocompatible materials that may be present in a hydrogel include, e.g., permeable configurations or morphologies, such as polyvinyl alcohol, polyvinylpyrrolidone and polyacrylamide, polyethylene oxide, poly(2-hydroxyethyl methacrylate); natural polymers such as polysaccharides, gums and starches; and include poly[α(4-aminobutyl)]-1-glycolic acid, polyethylene oxide, polyorthoesters, silk-elastin-like polymers, alginate, EVAc (poly(ethylene-co-vinyl acetate), microspheres such as poly (D,L -lactide-co-glycolide) copolymer and poly (L -lactide), poly(N-isopropylacrylamide)-b-poly(D,L -lactide), a soy matrix such as one cross-linked with glyoxal and reinforced with a bioactive filler, e.g., hydroxylapatite, poly(epsilon-caprolactone)-poly(ethylene glycol) copolymers, poly(acryloyl hydroxyethyl) starch, polylysine-polyethylene glycol, or agarose.

In one embodiment, the hydrogel includes poloxamers, polyacrylamide, poly(2-hydroxyethyl methacrylate), carboxyvinyl-polymers (e.g., Carbopol 934, Goodrich Chemical Co.), cellulose derivatives, e.g., methylcellulose, cellulose acetate and hydroxypropyl cellulose, polyvinyl pyrrolidone or polyvinyl alcohols, or combinations thereof.

In some embodiments, the hydrogel includes collagen, e.g., hydroxylated collagen, fibrin, polylactic-polyglycolic acid, or a polyanhydride. Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D,L-lactide-co-glycolide) block copolymers, polyglycolide, polylactides (PLLA or PDLA), poly(caprolactone) (PCL), or poly(dioxanone) (PPS).

In another embodiment, the biocompatible material includes polyethyleneterephalate, polytetrafluoroethylene, copolymer of polyethylene oxide and polypropylene oxide, a combination of polyglycolic acid and polyhydroxyalkanoate, gelatin, alginate, poly-3-hydroxybutyrate, poly-4-hydroxybutyrate, and polyhydroxyoctanoate, and polyacrylonitrilepolyvinylchlorides.

In one embodiment, the following polymers may be employed, e.g., natural polymers such as alginate, agarose, starch, fibrin, collagen, gelatin, chitin, glycosaminoglycans, e.g., hyaluronic acid, dermatan sulfate and chrondrotin sulfate, and microbial polyesters, e.g., hydroxyalkanoates such as hydroxyvalerate and hydroxybutyrate copolymers, and synthetic polymers, e.g., poly(orthoesters) and polyanhydrides, and including homo and copolymers of glycolide and lactides (e.g., poly(L-lactide, poly(L-lactide-co-D,L-lactide), poly(L-lactide-co-glycolide, polyglycolide and poly (D,L-lactide), pol(D,L-lactide-coglycolide), poly(lactic acid colysine) and polycaprolactone.

In one embodiment, the hydrogel comprises a poloxamer (polyoxyethylene, polyoxypropylene block copolymers, e.g., poloxamer 127, 231, 182 or 184).

Exemplary Components for Use in Hydrogels to Prevent, Inhibit or Treat PTOA

In one embodiment, the hydrogels useful in the compositions and methods of the invention are synthesized from a naturally occurring biodegradable, biocompatible, and hydrophilic polysaccharide, and a synthetic biocompatible polymer, such as poloxamers, polylactide ("PLA") polyglycolide ("PGA"), or poly(lactic acid co-glycolic acid) ("PLGA").

The composition of the invention that forms a hydrogel, e.g., a reverse temperature-sensitive hydrogel, includes a polysaccharide, including chemically cross linked polysaccharides and a synthetic or natural polymer, and a compound that reversibly inhibits complex I. One exemplary polysaccharide is hyaluronic acid (HA), a naturally occurring copolymer composed of the sugars glucuronic acid and N-acetylglucosamine. Specifically, HA, also named hyaluronan, is a high molecular weight ($10^5$-$10^7$ Da) naturally occurring biodegradable polymer that is an unbranched non-sulfated glycosaminoglycan (GAG) composed of repeating disaccharides (β-1,4-D-glucuronic acid (known as uronic acid) and β-1,3-N-acetyl-D-glucosamide). HA has an average MW of 4-5 million Da. HA can include several thousand sugar molecules in the backbone. HA is a polyanion that can self-associate and that can also bind to water molecules (when not bound to other molecules) giving it a stiff, viscous quality similar to gelatin. Hylans are cross-linked hyaluronan chains in which the carboxylic and N-acetyl groups are unaffected. The MW of hylan A is about 6 million Da. Hylans can be water-insoluble as a gel (e.g., hylan B).

HA's characteristics include its consistency, biocompatibility, hydrophilicity, viscoelasticity and limited immunogenicity. The hyaluronic acid backbone is stiffened in physiological solution via a combination of internal hydrogen bonds, interactions with solvents, and the chemical structure of the disaccharide. At very low concentrations, HA chains entangle each other, leading to a mild viscosity (molecular weight dependent). On the other hand, HA solutions at higher concentrations have a higher than expected viscosity due to greater HA chain entanglement that is shear-dependent. Thus, solutions containing HA are viscous, but the viscosity is tunable by varying HA concentration and the amount of crosslinking. In addition to the unique viscosity of HA, the viscoelasticity of HA is another characteristic resulting from entanglement and self-association of HA random coils in solution. Viscoelasticity of HA can be tied to molecular interactions which are also dependent on concentration and molecular weight.

Exemplary HA solutions for injection are shown in Table 1, and include include Synvisc® (high molecular weight HA due to crosslinking), Hyalgan® (sodium hyaluronate solution), and Orthovisc® (one of the viscosupplements with the highest HA concentration, which has lower viscosity than Synvisc®) (the properties of those are shown in Table 2).

TABLE 1

| Brand name (Generic name) | Molecular weight (kDa) |
|---|---|
| Durolane ® (Hyaluronic acid, 2%) | 1000 |
| Fermathron ® (Sodium hyaluronate, 1%) | 1000 |
| Hyalgan ® (Sodium hyaluronate, 1%) | 500-730 |
| NeoVisc ® (Sodium hyaluronate, 1%) | 1000 |
| Orthovisc ® (Sodium hyaluronate, 1%) | 1000-2900 |
| Ostenil ® (Sodium hyaluronate, 1%) | 1000-2000 |
| Supartz ® (Sodium hyaluronate, 1%) | 620-1170 |
| Suplasyn ® (Sodium hyaluronate, 1%) | 500-730 |
| Synvisc ® (Hylan G-F 20; Crosslinked HA) | 6000-7000 |

TABLE 2

| Brand name | Molecular weight (kDa) | Viscoelastic properties | |
|---|---|---|---|
| | | Elastic modulus (G') (Pa) at 2.5 Hz | Viscous modulus (G'') (Pa) at 2.5 Hz |
| Hyalgan ® (Uncrosslinked) | 500-730 | 0.6 | 3 |
| Orthovisc ® (Uncrosslinked) | 1000-2900 | 60 | 46 |
| Synvisc ® (Crosslinked polymer) | 6000-7000 | 111 ± 13 | 25 ± 2 |

Dextran is another polysaccharide and is formed primarily of 1,6-α-D-glucopyranosyl residues and has three hydroxyl groups per glucose residue that could provide greater flexibility in the formulation of hydrogels. Dextran has been widely used for many biomedical purposes, such as plasma expander and controlled drug delivery vehicle, because of its highly hydrophilic nature and biocompatibility. It is also possible to incorporate dextranase in order to facilitate biodegradation of dextran for the meeting of specific clinical needs.

In one embodiment, the hydrogel comprises a poloxamer. Poloxamers are nonionic triblock copolymers composed of a central hydrophobic chain of polyoxypropylene (poly (propylene oxide)) flanked by two hydrophilic chains of polyoxyethylene (poly(ethylene oxide)) (α-Hydro-ω-hydroxypoly (oxyethylene)$_a$ poly (ocypropylene)$_b$ poly (olxyethylene)$_a$ block copolymer, with two hydrophilic chains of ethylene oxide chains (PEO) that sandwich one hydrophobic propylene oxide chain (PPO) giving a chemical formula $HO(C_2H_4O)_a(C_3H_6O)_b(C_2H_4O)_a$). For example, poloxamer 407 is a triblock copolymer consisting of a central hydrophobic block of polypropylene glycol flanked by two hydrophilic blocks of polyethylene glycol. Exemplary poloxamers include but are not limited to polyethylene-propylene glycol copolymer, e.g., Supronic, Pluronic or Tetronic a non-ionic triblock copolymer.

The common representation of Poloxamer is indicated as 'P' succeeded by three digits where the first two digits are to be multiplied by 100 and that gives the molecular mass of the hydrophobic propylene oxide and the last digit is to be multiplied by ten that gives the content of hydrophilic ethylene oxide in percentage. Poloxamers usually have an efficient thermoreversible property with characteristics sol-gel transition temperature. Below the transition temperature it is present as a solution and above this temperature the solution results in interaction of the copolymer segment which leads to gelation. Poloxamers are non-toxic and non-irritant.

TABLE 3

| Poloxamer | Pluronic | Physical form | Ethylene oxide units $(n)^a$ (a) | Propylene oxide units $(n)^a$ (b) | Average molecular mass PhEur 2005; USPNF 23 | Weight % of Oxyethylene | |
|---|---|---|---|---|---|---|---|
| | | | | | | PhEur 2005 | USPNF 23 |
| 124 | L 44 | Liquid | 10-15 | 18-23 | 2090-2360 | 44.8-48.6 | 46.7 ± 1.9 |
| 188 | F 68 | Solid | 75-85 | 25-40 | 7680-9510 | 79.9-83.7 | 81.8 ± 1.9 |
| 237 | F 87 | Solid | 60-68 | 35-40 | 6840-8830 | 70.5-74.3 | 72.4 ± 1.9 |
| 338 | F108 | Solid | 137-146 | 42-47 | 12700-17400 | 81.4-84.9 | 83.1 ± 1.7 |
| 407 | F127 | Solid | 95-105 | 54-60 | 9840-14600 | 71.5-74.9 | 73.2 ± 1.7 |

Compounds that reversibly inhibit complex I include but are not limited to amobarbital or derivatives thereof, metformin or derivatives thereof, or adenosine diphosphate ribose analogs that disrupt NADH binding. However, non-reversible inhibitors of complex I, e.g., Rotenone, Piericidin A or Rolliniastatin 1 and 2, in low doses, may also have some benefit to cartilage after injury as a result of altering ROS.

Formulations and Dosages

The components of the composition of the invention can be formulated as pharmaceutical compositions and administered to a mammalian host, such as a human patient in a variety of forms adapted to the chosen route of administration. In one embodiment, the components of the composition are locally administered to a site of cartilage damage or suspected cartilage damage, or is administered prophylactically.

In one embodiment, the components of the composition may be administered by infusion or injection. Solutions may be prepared in water, optionally mixed with a nontoxic surfactant. Dispersions may also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion may include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle may be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars, buffers or sodium chloride.

Sterile injectable solutions may be prepared by incorporating the active agent in the required amount in the appropriate solvent with various other ingredients, as required, optionally followed by filter sterilization. In the case of sterile powders for the preparation of sterile injectable solutions, the methods of preparation include vacuum drying and the freeze drying techniques, which yield a powder of the active ingredient plus any additional desired ingredient present in the previously sterile-filtered solutions.

Useful solid carriers may include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as antimicrobial agents can be added to optimize the properties for a given use. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compound(s) in the composition can be determined by comparing their in vitro activity and in vivo activity in animal models thereof. Methods for the extrapolation of effective dosages in mice, and other animals, to humans are known to the art; for example, see U.S. Pat. No. 4,938,949.

Generally, the concentration of the compound(s) in a liquid composition, may be from about 0.1-25 wt-%, e.g., from about 0.5-10 wt-%. The concentration in a semi-solid or solid composition such as a gel or a powder may be about 0.1-5 wt-%, e.g., about 0.5-2.5 wt-%.

The amount of the compound for use alone or with other agents may vary with the type of hydrogel, route of administration, the nature of the condition being treated and the age and condition of the patient, and will be ultimately at the discretion of the attendant physician or clinician.

The components of the composition may be conveniently administered in unit dosage form; for example, containing 5 to 1000 mg, conveniently 10 to 750 mg, or conveniently 50 to 500 mg of active ingredient per unit dosage form.

In general, however, a suitable dose may be in the range of from about 0.5 to about 100 mg/kg, e.g., from about 10 to about 75 mg/kg of body weight per day, such as 3 to about 50 mg per kilogram body weight of the recipient per day, for example in the range of 6 to 90 mg/kg/day, e.g., in the range of 15 to 60 mg/kg/day.

The invention will be described by the following non-limiting example.

EXAMPLE

In one embodiment, an injectable temperature-sensitive composite hydrogel is employed where the hydrogel is liquid during injection, then gelates when inside the body (gelates at human body temperatures). In one embodiment, the injectable temperature-sensitive composite hydrogel (e.g., one having hyaluronic acid, such as Gel One which is chemically cross-linked and has a high molecular weight, and F127) is employed to deliver a therapeutic, for instance, the hydrogel is loaded with amobarbital which reversibly inhibits the respiratory enzyme Complex I, a key mediator of chondrocyte injury after impact. The hydrogel becomes firm once injected (preventing leakage from the joint) allowing the therapeutic to be retained in the joint region, for example, for about 3 days after injection into the site of articular injury. In one embodiment, the hydrogel comprises 17% (w/v) F-127 and 0.2% (w/v) HA, and is loaded with 2.5 mM amobarbital. The temperature-sensitive hydrogel fixes the amobarbital, which prevents chondrocyte death, at the site of injury.

Figure 4:
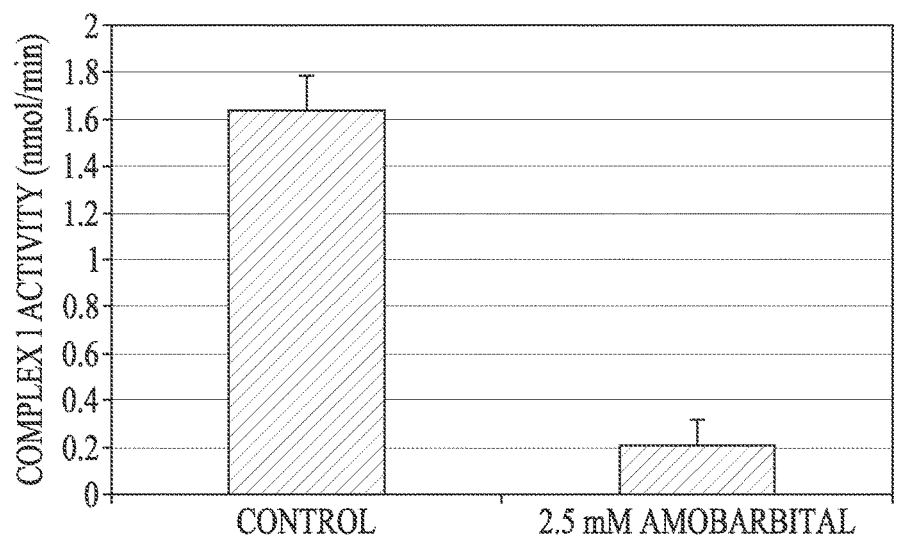
FIG. 4 shows complex I activity in the presence or absence of amobarbital.

FIG. 4 shows that amobarbital directly inhibits the biochemical activity of complex I of the electron transport chain in chondrocytes.

REFERENCES

Martin et al., *Journal of Bone and Joint Surgery*, 91A:1890.
Goodwin et al., *Journal of Orthopaedic Research*, 28(8): 1057.
Wolff et al., *Journal of Orthopaedic Research*, 31:191 (2015).
Sauter et al., *Journal of Orthopaedic Research*, 30:593.
Jubeck, *Arthritis Rheum.*, 58(9):2809.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An injectable composition comprising a hydrogel comprising hyaluronic acid having a molecular weight of 1 million Da or greater and 15% wt/vol to about 20% wt/vol F127, and an amount of amobarbital or a derivative thereof effective to inhibit post-traumatic osteoarthritis.

2. The composition of claim 1 wherein the hyaluronic acid is present in the composition from about 0.01% (wt/vol) and up to about 2.0% (wt/vol).

3. The composition of claim 1 wherein the hyaluronic acid is present at about 0.2% wt/vol to about 1.0% wt/vol.

4. The composition of claim 1 wherein the hydrogel further comprises N-isopropyl acrylamide polymer, a polysaccharide other than hyaluronic acid, hydroxypropylcellulose, karya gum, guar gum, gellan gum, alginate, ethylhydroxyethylcellulose, poly(ethyleneoxide-b-propylene oxide-b-ethylene oxide), a PLURONICS® polymer, a poly(ethylene glycol)/poly(D,L-lactic acid-co-glycolic acid) block co-polymer, a polyphosphazine, a polyacrylate, a TETRONICS™ polymer, or a polyethylene oxide-polypropylene glycol block copolymer.

5. The composition of claim 1 wherein the derivative comprises pentobarbital, secobarbital, phenobarbital, or barbital.

6. The composition of claim 1 wherein the amount inhibits mitochondrial dysfunction or chondrocyte energy dysfunction.

7. The composition of claim 1 wherein the amobarbital or a derivative thereof scavenges mitochondrial oxidants or prevents their formation, or stimulates glycolytic ATP production.

8. A method to inhibit chondrocyte death and improve chondrocyte function after injury in a mammal, comprising locally administering an effective amount of the composition of claim 1 to an injured joint of a mammal.

9. The method of claim 8 wherein the composition is injected.

10. The method of claim 8 wherein the composition comprises amobarbital, pentobarbital, secobarbital, or phenobarbital.

11. The method of claim 8 wherein the amount inhibits mitochondrial dysfunction or chondrocyte energy dysfunction.

12. The method of claim 8 wherein the administration reduces ROS production in cartilage.

13. The method of claim 8 wherein the administration is within 4 days of the injury.

14. The method of claim 8 wherein the administration is with 12 hours of the injury.

15. The method of claim 8 wherein the administration is with 5 hours of the injury.

16. The method of claim 8 wherein the injury is a knee, hip, ankle or elbow injury.

17. A method to inhibit post-traumatic osteoarthritis in a mammal, comprising locally administering an effective amount of the composition of claim 1 to a mammal at risk of posttraumatic osteoarthritis as a result of injury to cartilage.

18. The method of claim 17 wherein the composition is injected.

19. The method of claim 17 wherein the composition comprises amobarbital, pentobarbital, secobarbital, or phenobarbital.

20. The method of claim 17 wherein the administration is within 4 days of the injury.

21. The method of claim 17 wherein the mammal has an injured joint.

22. The method of claim 17 wherein the administration is with 12 hours of the injury.

23. The method of claim 17 wherein the administration is with 5 hours of the injury.

24. The method of claim 17 wherein the injury is a knee, hip, ankle or elbow injury.

25. The method of claim 17 wherein the mammal is a human.

* * * * *